United States Patent [19]

Chamuel

[11] Patent Number: 4,461,178
[45] Date of Patent: Jul. 24, 1984

[54] ULTRASONIC AIRCRAFT ICE DETECTOR USING FLEXURAL WAVES

[75] Inventor: Jacques R. Chamuel, Framingham, Mass.

[73] Assignee: The Charles Stark Draper Laboratory, Inc., Cambridge, Mass.

[21] Appl. No.: 364,902

[22] Filed: Apr. 2, 1982

[51] Int. Cl.³ .................. G08B 19/02; G01N 29/00
[52] U.S. Cl. .................................. 73/599; 340/582; 367/75
[58] Field of Search .................. 73/599; 340/582; 367/35, 75

[56] References Cited

U.S. PATENT DOCUMENTS

| | | | |
|---|---|---|---|
| 2,439,130 | 4/1948 | Firestone | 73/599 |
| 3,240,054 | 3/1966 | Roth | 340/582 |
| 3,477,278 | 11/1969 | Lynnworth | 73/599 |
| 3,775,739 | 11/1973 | Vogel | 367/75 |
| 4,254,479 | 3/1981 | Wiley | 367/35 |
| 4,335,613 | 6/1982 | Lukkala | 73/599 |

FOREIGN PATENT DOCUMENTS 775013  5/1957  United Kingdom ................. 340/582

OTHER PUBLICATIONS

"Acoustic Character Logs and Their Applications in Formation Evaluation", Pickett, *Journal of Petroleum Technology*, Jun. 1963, pp. 659–667.

*Primary Examiner*—Howard A. Birmiel
*Attorney, Agent, or Firm*—Weingarten, Schurgin, Gagnebin & Hayes

[57] ABSTRACT

A system for the detection of wing icing by monitoring variations in flexural waves transmitted through the outer plate material of an aircraft airfoil. The flexural waves in the plate of the wing airfoil are more subject to variation from the accumulation of ice on the wing than the compressional waves. The flexural waves are detected apart from the compressional waves, which tend to remain relatively constant, to provide an indication of icing. Changes in amplitude, phase or dispersion characteristics of the flexural waves are detected to indicate ice buildup, and, in one embodiment, these values are ratioed to the corresponding levels in the compressional wave in order to provide compensation for variations other than ice buildup. The ultrasonic waves may be coupled directly from a transducer to the airfoil plate or via an ultrasonic waveguide interposed between the transducer and the plate. The receiver for the ultrasonic waves to be detected may be positioned to receive direct flexural waves transmitted over a distance through the plate or flexural waves reflected from reflecting boundaries in the plate.

21 Claims, 17 Drawing Figures

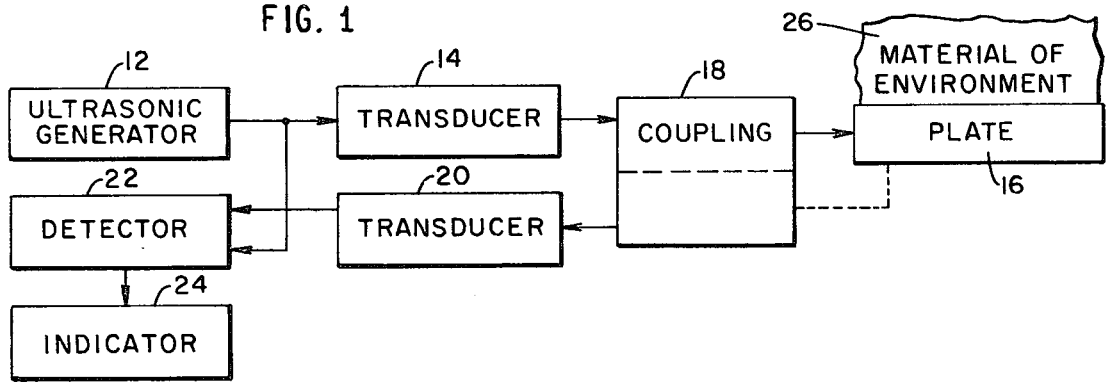
FIG. 1
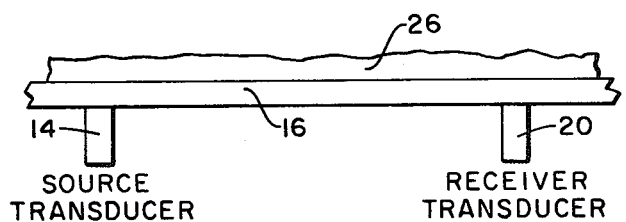
FIG. 2
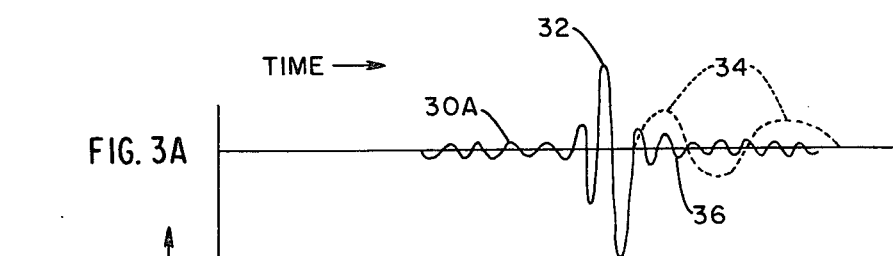
FIG. 3A
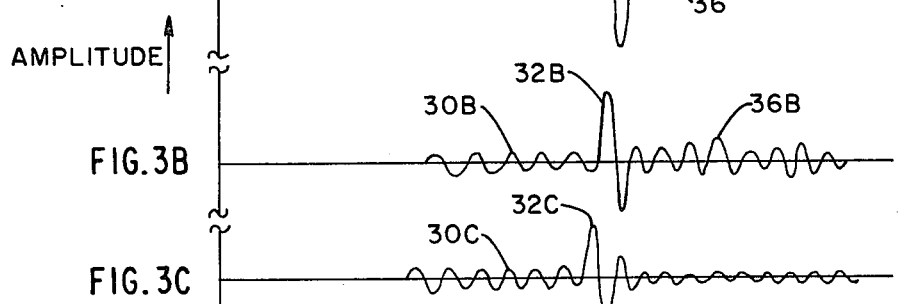
FIG. 3B
FIG. 3C
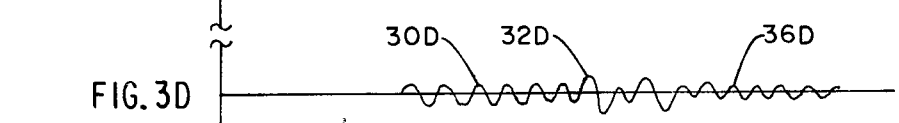
FIG. 3D
FIG. 3E
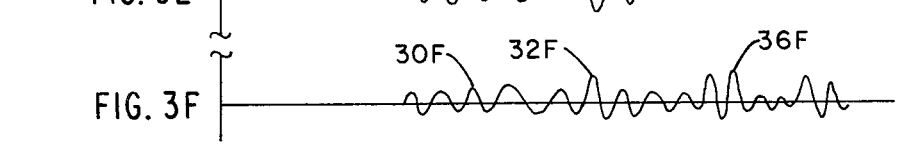
FIG. 3F

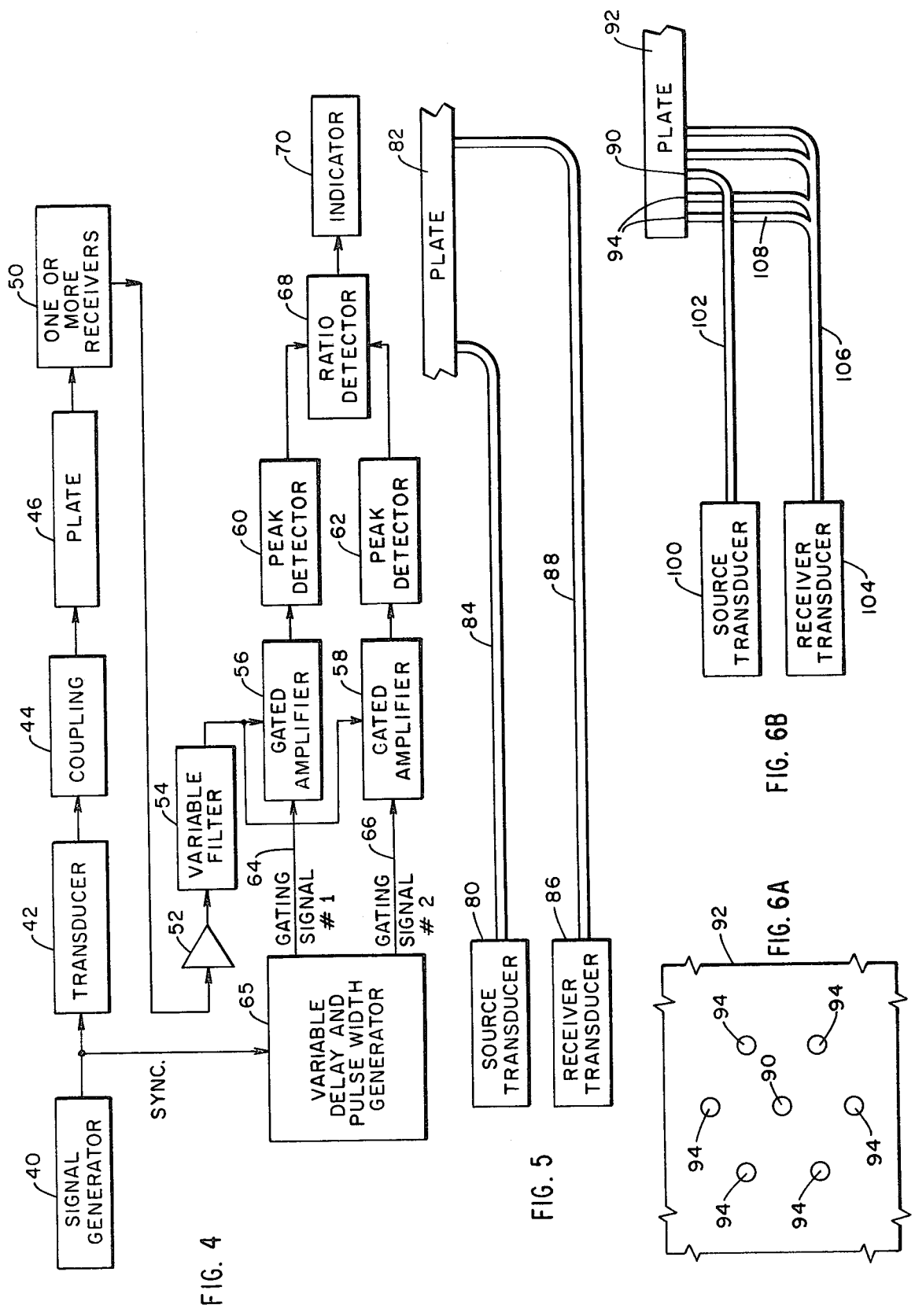

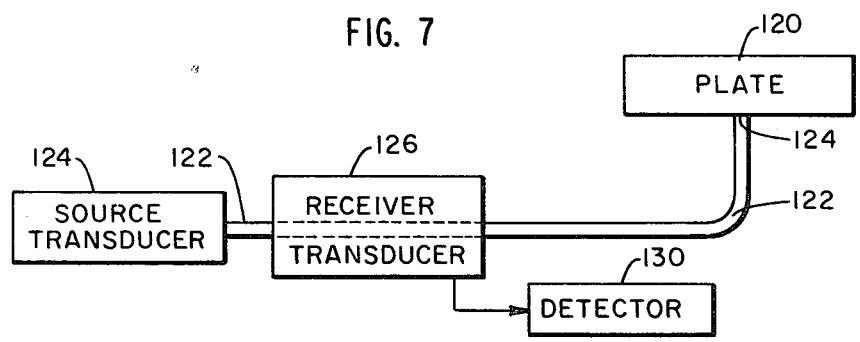
FIG. 7
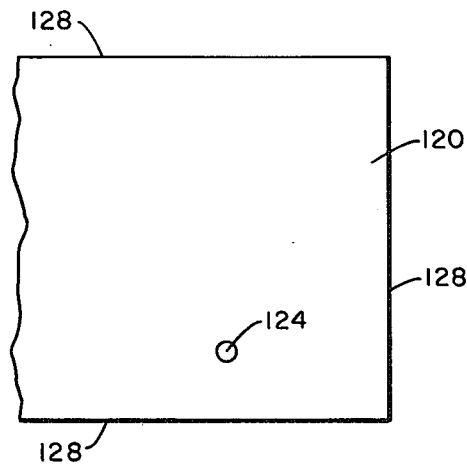
FIG. 8
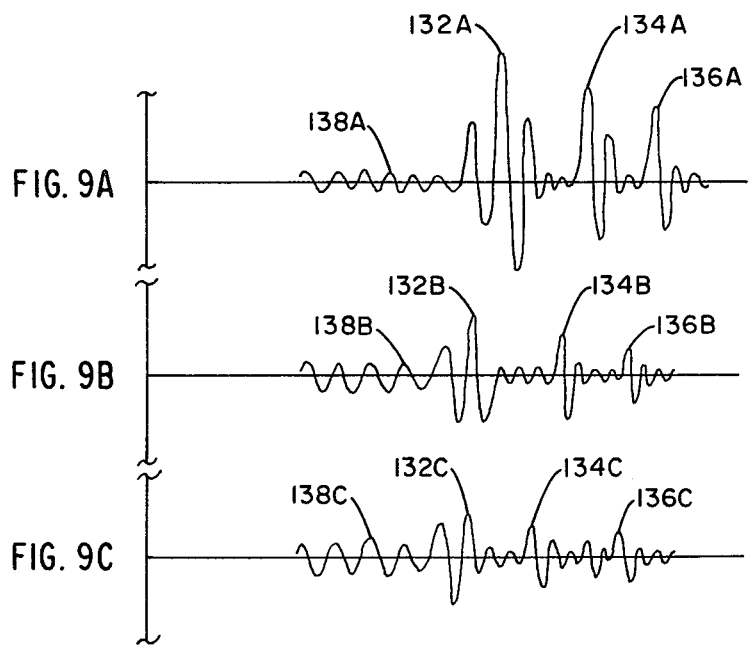
FIG. 9A
FIG. 9B
FIG. 9C

ULTRASONIC AIRCRAFT ICE DETECTOR USING FLEXURAL WAVES

FIELD AND BACKGROUND OF THE INVENTION

The detection of the accumulation of an undesirable layer on a surface, particularly in the case of wing icing, is an area of interest. The reliable detection of this buildup as well as the ability to discriminate between various forms of accumulation are important objectives for such a system.

Very little ice is needed to impair the flying ability of aircraft, particularly during low speed flight. Many detection schemes have been proposed for determining the presence of a layer of ice on wing airfoil surfaces but reliable detection of this situation, without having devices mounted externally on the wing, is difficult. The presence of external instrumentation which would facilitate detection is undesirable from the standpoint of maintaining a smooth airflow across the wing during flight. This essentially restricts the placement of instrumentation, if large portions of the wing are to be monitored, to structures inside the wing. Even there, the addition of large amounts of weight to the wing structure are to be avoided particularly at remote wing points where leverage augments the effect of such weights. Furthermore, the addition of electrical circuits and heaters in the vicinity of fuel may not be too desirable in some applications.

If sound waves are applied to the wing airfoil plate and then detected, either at some remote point or after reflection of the sound energy from reflecting barriers in the airfoil plate, two problems are immediately encountered in attempting to detect ice. In the first, sonic wave used for detection purposes may be submerged in sound energy generated by aircraft machinery, such as engines, compressors, and other devices normally encountered on a large passenger airplane. In addition, the compressional component of the sonic wave is affected relatively little by even significant accumulations of ice.

Precipitation can accumulate on an aircraft wing in a variety of different forms which include a layer of water, a layer of frost, a layer of slush, a layer of snow, a layer of ice of variable thickness which may, or may not, be frozen to the wing plate. Flight decisions made by the pilot or others may depend upon the detection of only only the presence of an accumulation, but its nature, location and the degree to which it is attached to the wing surface. Furthermore, the cost of de-icing airplanes before take-off may be reduced by minimizing the number of deicings by continuously monitoring the aircraft condition.

SUMMARY OF THE INVENTION

In accordance with the teaching of the present invention, a detector for the accumulation of material, such as ice on a wing, is provided in which ultrasonic waves are applied to or generated in the surface upon which the accumulation is expected and flexural components of the waves are detected after transmission of the ultrasonic waves through a region of the surface material. The flexural component, which has been shown to be sensitive to accumulations on the surface, is detected apart from the compressional component of the wave which typically travels faster.

In one embodiment for detecting aircraft wing icing, an ultrasonic signal is generated and applied to the airfoil plate by an ultrasonic transducer which typically is bonded directly to the inner surface of the wing airfoil plate. One or more further receiver transducers are arrayed along, and coupled to, the inner surface of the wing plate to receive the ultrasonic wave energy applied to the plate by the first transducer. The ultrasonic wave as thus received, is converted to a signal and applied to a detector to determine variations in the flexural component of the signal. Preferably, this signal is first filtered to remove lower frequency components in the spectral regions where substantial sonic wave energy induced by normal aircraft machinery is present. It is also preferable that the filter remove lower frequencies of the flexural wave in the case of broadbanded ultrasonic energy applied, for example, by a pulse source. Because substantial frequency dispersal occurs in the flexural wave, this tends to concentrate the received flexural wave energy in the filtered signal within a more narrow, temporal, and spectral region. Variations in this received flexural wave are detected by amplitude, phase, or frequency techniques. Amplitude variations are typically detected by a peak detector, while phase or frequency variations are also, or alternatively, detected using appropriate phase and frequency detection techniques. An indicator is provided to show variations in the detected magnitude.

Each aircraft installation is likely to have a different ultrasonic response characteristic. Thus, typically, each installation will initially be calibrated and preferred operating frequencies and filtration characteristics be established empirically, based upon considerations of sensitivity among other factors. Once this initial calibration is made, future variations in the indicated detector output identify the amount and nature of accumulations of ice on the aircraft wing surface.

The ultrasonic signal originally generated may be in the form of a single pulse, a burst of a preselected frequency, a continuous wave, or a frequency chirp. In addition, the ultrasonic energy produced or received by the transducers may be coupled directly to the wing or transmitted to the wing through ultrasonic waveguides permitting location of the transducers outside of the wing structure and thereby avoiding the addition of significant weight to the wing from the transducers and associated electrical cables and circuits.

In some applications, the sound energy generated by normal aircraft components such as engines, compressors and generators, may be of an appropriate characteristic to be used as the sound energy detected in lieu of separately generated sound waves.

In addition, the source and receiving transducers may be physically coupled to the same point on the plate of the aircraft wing with the receiver and associated detection electronics operative to sense waves reflected from reflecting regions of the aircraft wing plate.

In the case where the accumulation on the wing plate is not adhered to the exterior surface, for example where a sheet of ice freely floats on a thin film of water, the effects of the ice on dispersion of the flexural waves is reduced, however the flexural waves will be attenuated. Where a layer of ice of some thickness is adhered to the wing surface, shear forces can be maintained between the wing surface and the ice coating resulting in a variation in the shear wave component of the received signal. The appearance of these waves can be detected to provide an indication of the degree of bonding between the ice coating and the wing surface. This effect can be elsewhere used in practicing the invention to detect bonding between laminations.

Other applications can be made of the invention in detection of the accumulation of a wide variety of material on thin walled members where the thickness is less than the wavelength of the ultrasonic waves used. Accordingly, the invention may be used to detect accumulations on hollow pipes or tubes.

BRIEF DESCRIPTION OF THE DRAWING

These and other features of the invention are more fully set forth below in the solely exemplary, detailed description and accompanying drawing of which:

FIG. 1, is a block diagram of a detection system for sensing accumulations of a material on a plate (or thin walled structure);

FIG. 2, is a diagramatic view illustrating one possible arrangement for transducers for use in the block diagram of FIG. 1;

FIGS. 3A-3F, are waveform diagrams illustrating the variation in signal output of the block diagram of FIG. 1 for different accumulations of ice on a plate;

FIG. 4, is a detailed block diagram of one embodiment for detecting the accumulation of ice on a plate surface;

FIG. 5, is a block diagram illustrating an alternative form of coupling between transducer and plate;

FIGS. 6A and 6B, illustrate a possible array of sites for coupling sound to and from a plate;

FIG. 7, illustrates a further alternative coupling system using a unitary waveguide having both source and receiving transducers coupled thereto;

FIG. 8, illustrates a coupling site for a waveguide of the type of FIG. 7 on a plate having sound reflecting boundaries;

FIGS. 9A-9C, are waveform diagrams illustrating typical signals produced by the configurations of FIG. 7 and FIG. 8;

DETAILED DESCRIPTION

The present invention contemplates a technique for detecting the amount and nature of an accumulation of material on a thin walled member such as a plate or tube by sensing the effect of the accumulation on ultrasonic waves, and in particular flexural waves (particularly the shear vertical component) as distinguished from compressional waves, transmitted through the plate. To permit flexural waves to be transmitted by the member, its thickness is kept below a certain dimension which is a function of the wavelength of the ultrasonic waves. Typically the thickness will be less than the wavelength. The invention has particular application to detecting wing icing.

A system for accomplishing this objective is shown in block diagram form in FIG. 1. An ultrasonic signal generator 12 applies an output to a transducer 14. The signal generator 12 will typically generate signals at a frequency which is distinct from the frequencies of vibrational sound generated by equipment normally associated with the structure, typically an aircraft, on which the accumulation is to be sensed. The frequency will also be selected for a desired or optimal sensitivity of the system since, due to the structural features of a complex mechanism such as an aircraft, the actual response of the structure to ultrasonic waves will be different at different frequencies. This variation is attributable to both the nature of the plate on which the ice accumulates as well as the nature of the underlying structure. Such optimization is normally empirically accomplished.

The signal provided by the generator 12, will typically be a pulse for the exemplary purposes of the disclosure described herein though it is contemplated that the generated signal may also be a burst of single frequency energy, a continuous wave, or a frequency chirped signal.

The transducer 14 converts the signal energy into an acoustical wave which is applied to a plate 16, such as the skin of an aircraft wing, through a coupling 18 which may be either a direct mechanical coupling of the transducer 14 to the plate 16 or an acoustic wave coupler or waveguide. Ultrasonic energy in the plate 16 after passing through a portion of the plate, is sensed by a further transducer 20 which is coupled to plate 16 either directly or through a coupling system 18. Coupling system 18 is either the same or a distinct coupling system from the coupling system 18 used for the transducer 14. The transducer 20 provides an output signal to a detector 22. Typically the detector 22 includes a filter to respond to a predetermined frequency or frequency range in the signal from the transducer 20. The output of the detector 22 is applied to an indicator 24 which can be used to provide a quantitative indication of the amount of accumulation of the material 26 on the plate 16, and further to indicate its nature.

With reference to FIG. 2, a typical arrangement is shown where source and receiver transducers 14 and 20 are in direct contact with plate 16 which has thereon a layer 26 of ice. The layer 26 of ice will affect the signal waveforms produced by the transducer 20, as illustrated in FIGS. 3A-3F, depending upon the existence, amount, and nature of the layer 26. The waveforms illustrated in FIG. 3A-FIG. 3F apply to the case where the signal from ultrasonic generator 12 is a single pulse. The waveform produced by the transducer 20 with no material 26 on the plate 16 is illustrated in FIG. 3A. This waveform includes an initial portion 30 which corresponds to the compressional wave transmitted through the plate 16 from the source transducer 14. Subsequent to the compressional wave 30, a larger spike 32 corresponds to the first receipt of the flexural wave transmitted by plate 16. Typically the flexural component 32 will have a tail portion 34 in which the frequency gradually increases as a result of frequency dispersion of the flexurally transmitted frequency components in the pulse. For purpose of the waveform illustrated in FIG. 3A this signal is filtered to eliminate these low frequency components. FIG. 3B illustrates the case where a film of water is applied to the upper surface of the plate 16. As can be seen, in this case there is an attenuation of the flexural wave component as indicated in the portion 32B while the initial compressional wave is attenuated to a lesser extent. In FIG. 3C, representing a thin frost layer, further attenuation of the flexural component as shown by waveform 32C, while the compressional wave remains basically unchanged. In FIG. 3D a situation is shown in which a thin, typically 3.5 mm, thickness of ice exists on the plate 16 showing a further, dramatic attenuation of the flexural wave portion 32D while the compressional portion 30D remains substantially unchanged. FIGS. 3E and 3F represent a thick ice layer, typically 21 mm, respectively free to slide and frozen on the plate 16. In the case of the layer free to slide, the flexural wave remains greatly attenuated relative to the compresional wave and the tail portion 36E remains substantially unchanged. Where the thick layer is frozen to the plate 16, however, as shown in FIG. 3F, not only is the flexural wave 32F greatly attenuated, while the compressional wave 30F remains substantially the same, but additional signal peaks are shown in tail portion 36F. With a frozen layer, coupling of acoustic waves through shear forces between the plate and the frozen layer takes place, with the frozen layer acting as a delay line to produce a notable signal peak substantially delayed by the additional path length through the large frozen ice layer 26.

As can be seen from FIGS. 3A–3F, significant variations occur within the received waveform as produced by the transducer 20, after filtering, each with characteristics depending upon the nature, thickness, and bonding of an accumulation of ice 26 on the plate 16. Processing electronics are used within the detector 22 in order to distinguish the various situations represented by FIGS. 3B–3F. One example of such processing is illustrated in FIG. 4 in which the amplitude of the flexural component 32 is detected to provide an indication of the existence of ice. In order to improve the accuracy of the determination, advantage is taken of the situation illustrated in the waveform diagrams of FIGS. 3A–3B which show that the compressional wave portion 30 remains substantially unchanged in magnitude while the magnitude of the flexural portion 32 greatly varies with the magnitude and bonding of the ice layer 26.

The system of FIG. 4 includes a signal generator 40 which for convenience will be assumed to be operating in the pulse mode as indicated above. The generator 40 drives a single transducer 42 which, via coupling 44 that is either a direct mechanical attachment or waveguide, excites a plate 46 with ultrasonic vibrations corresponding to the frequencies in the pulse from generator 40. One or more receiver transducers 50 are coupled to the plate 46, either directly or remotely through a waveguide, to provide an output signal representative of the received ultrasonic energy. A buffer amplifier 52 responds to this signal and applies its output to a variable filter 54. The filter 54 is typically made variable in the system so that the final installation, such as in an aircraft, can have the frequency to which the detector electronics will respond adjusted to account for the specific characteriestics of each structure. In this manner, the sensitivity of the system to ice can be optimized. The output of the variable filter 54 is applied to first and second gated amplifiers 56 and 58 with their outputs applied to respective peak detectors 60 and 62. The gated amplifiers 56 and 58 have further inputs from respective first and second delayed pulses on lines 64 and 66 respectively from a variable delay and pulse width generator 65. These delayed pulses are synchronized with the signal generator 40 to gate the amplifiers 56 and 58. In this manner, the gates 56 and 58 are activated to pass to the peak detectors 60 and 62 the filtered, acoustic signal from plate 46 only during those time periods in which the compressional and flexural portions respectively occur.

The peak detectors 60 and 62 typically respond to indicate the peak magnitude of the compressional and flexural portions and to hold those values for application to a ratio detector 68 which provides an output signal to an indicator 70 corresponding to the ratio of the flexural peak to the compressional peak. While it is possible to provide an indication of ice accumulation without the use of the ratioing technique illustrated in FIG. 4, by ratioing the flexural peak to the compressional peak a form of automatic calibration is provided which will compensate for any variations in system gain which may occur. As noted above, the compressional wave is substantially less sensitive to the accumulation of ice than is the flexural wave so that the ratio of the two not only compensates for system gain characteristics but still is a reliable indication of the magnitude of the flexural wave and therefore of the presence and magnitude, as well as bonding, of the ice layer 26 on the plate 16.

FIG. 5 illustrates the use of a waveguide coupling between transducer and plate. In particular a source transducer 80, which may be of a type known in the art, is coupled to a plate portion 82 representing, typically, a wing section of an aircraft, through a waveguide 84. Similarly, a receiver transducer 86 is coupled to receive ultrasonic energy from the plate 82 through a sonic waveguide 88. The waveguides 84 and 88 may typically be a long wire such as 0.06 inch diameter nickel wire of a desired distance, 12 feet being one exemplary dimension. The use of the waveguides 84 and 88 permits the location of the source and receiver transducers 80 and 86 remotely from the plate 84 which, in the case of an aircraft wing, reduces the weight required to be carried by the wing itself and also reduces the electrical circuits in the wing. This in turn reduces the stress and leverage which occurs from increasing the weight of wing sections.

Because the energy applied from a source transducer to the wing plate will typically spread in all directions from the source, it may be desirable to place receivers about a circle centered around the point where the source energy is applied, either by direct mechanical coupling from the transducer or by using a waveguide mechanically bonded to the plate and transducer. The situation is illustrated in FIG. 6A in which a spot 90 corresponds to the point at which ultrasonic energy is applied to a plate 92. A set of receiver spots 94 are placed on a circle about the spot 90 at a distance of approximately a foot from the source spot 90.

One embodiment for coupling the received energy at the spots 94 to a receiver transducer is illustrated in FIG. 6B. As shown there a source transducer 100 utilizes a waveguide 102 to apply ultrasonic energy to spot 90 of the plate 92. A receiver transducer 104 receives energy from the ultrasonic vibrations in the plate 92 through a waveguide 106 having branches 108 coupled mechanically to each of the individual spots 94. This permits the single receiver transducer 104 to respond to the ultrasonic energy distributed in all directions about the source spot 90. The waveform produced by the transducer 104 from the combined vibrational signals may look significantly different from the waveforms of FIGS. 3A–3F but the same concept of compressional and flexural waves and their difference in time of arrival will apply. The length of the individual branches 108 may be adjusted to phase the flexural components in a desired manner.

In lieu of separating the point at which ultrasonic energy is applied to and received from a plate, those points may be combined as illustrated in FIG. 7. As shown there, a plate 120 has an ultrasonic waveguide 122 mechanically bonded to it at a point 124. The waveguide 122 is typically a wire having at an opposite end a source transducer 124. Magnetostrictive or electromagnetic transduction in the wire metal can be used to generate or detect the waves. Transducer 124 is typically a magnetic coil separated from a receiver transducer 126, also typically a magnetic coil wound about magnetostrictive wire 122.

The plate 120, as illustrated in FIG. 8, will typically have boundaries 128 at which reflections of ultrasonic waves take place. The receiver transducer 126 applies a signal to a detector system 130 which thus typically appears illustrated in FIGS. 9A–9C. In FIG. 9A, the reflection from the various boundaries 128 will typically produce a set of time separated flexural signal waveforms 132A, 134A, and 136A. These waveforms can be processed by amplitude, frequency or phase detection techniques as indicated above and may use a ratioing of such detection with respect to an initially received portion 138, representing the compressional part of the signal wave. As illustrated in FIGS. 9B and 9C, the flexural portions 132B, 132C, 134B, 134C, 136B and 136C will experience attenuation effects in traversing the material of the plate 120 under the influence of an accumulation of a material on its surface and representative of its nature and magnitude. The compressional portions 134A, 138B and 138C will not experience the same level of attenuation.

The circuitry of FIG. 4 may be varied with the addition of further delayed pulses and corresponding gated amplifiers in order to sample several time segments of the flexural waves and to process them by techniques as appropriate.

The transducers, whether for purposes of applying energy in the form of ultrasonic waves to the various plates of the wing surface or for receiving such energy can be of any known type including, magnetostrictive, piezoelectric, electromagnetic, electrostatic, laser and purely mechanical (hammer-like). Magnetostrictive transducers pose certain advantages for the present application in view of the ease with which waveguide couplers can be utilized with such transducers. Direct attachment of transducers may be by bolt, solder, rivet or other means.

The various detector schemes for use with the present invention include amplitude detection, with or without signal delaying and ratioing, spectrum analysis with or without ratioing. Filtration, variable or fixed, can be used to limit the receiver transducer output sensitivity to a particular frequency or frequencies. In addition, the phase of the receiver transducer output can be compared to the phase of the originally generated signal and its variation determined as an indication of icing.

The invention may also be applied to the detection of bonding quality between layers or the detection of characteristics of a layer deposited on a substrate. In the case of bonding quality, the effects of shear coupling between the layers can be detected as described above.

Other modifications are possible within the disclosure of the invention, the actual scope being solely as indicated in the following claims.

What is claimed is:

1. A system for detecting the presence of ice and water on a thin-walled surface comprising:
    means for generating a signal;
    a transmitting transducer producing an acoustic signal according to said generated signal;
    means for coupling said acoustic signal to said thin-walled surface providing acoustic signal propagation thereon in at least two modes:
    a receiver transducer providing an electrical signal corresponding to a received acoustic signal;
    means for coupling said receiver transducer to said thin-walled surface, coupling the propagated acoustic signal to said receiver transducer;
    receiver means providing a first and a second signal, each signal corresponding to a different mode of propagation of said acoustic signal;
    means for providing a signal corresponding to a ratio between the amplitudes of said first and said second signal; and
    indicator means for providing an alarm signal when the signal provided by said ratio signal means exceeds a predetermined threshold indicating the presence of one of ice and water on said thin-walled surface.

2. The system of claim 1, wherein said signal means for generating provides an ultrasonic signal.

3. The system of claim 1, wherein said signal means for generating produces a signal comprising at least one of a pulse, a burst, a continuous wave, and a chirp signal characteristic.

4. The system of claim 1 wherein said transmitter transducer comprises a mechanical vibration transducer including one of a piezoelectric crystal, a magnitostrictive element, an electromagnetic transducer, an electrostatic transducer, a mechanical transducer and a laser.

5. The system of claim 1 wherein said receiver transducer means comprises a means to couple to a plurality of surface locations.

6. The system of claim 1 wherein said system includes waveguide means for coupling the acoustic signal to at least one of said transmit and receive transducer.

7. The system of claim 6, wherein said waveguide comprises a wire element.

8. The system of claim 6, wherein said waveguide further comprises a plate means interposed between said aircraft surface and one of said transmit and receive transducer.

9. The system of claim 1, wherein said receiver means includes:
    time gating amplifier means to selectively provide said first and said second signals according to specific time intervals; and
    peak detector means providing a signal corresponding to the peak level of the received acoustic signal at said time intervals, wherein said specific time intervals are synchronized to said transmitted acoustic signal.

10. The system of claim 1, wherein said receiver means further includes a selective filter means.

11. The system of claim 10, wherein at least one of said first and said second signal corresponds to a flexural component of the propagated acoustic signal.

12. The system of claim 1, wherein the receiver transducer comprises a mechanical vibration transducer including one of a piezoelectric crystal, a magnetostrictive element, an electromegnetic transducer, a mechanical transducer, and a laser.

13. A method of detecting the presence of ice and water on a thin-walled surface circuit, comprising the steps of:
    applying sound energy to said thin-walled surface;
    sensing the propagation of the sound energy over a distance on said thin-walled surface and providing a corresponding sensed signal;
    separating said sensed signal into a first and second signal, each said signal corresponding to a different wave propagation mode;

determining the ratio between the amplitudes of said first and second signal and providing a ratio output signal; and indicating the presence of a loading condition according to the relative amplitude of said ratio output signal.

14. The method of claim 13, wherein said step of applying includes the step of generating an ultrasonic signal.

15. The method of claim 14, wherein said step of generating an ultrasonic signal includes at least one of piezoelectric transduction, magnetostrictive transduction, electromagnetic transduction, electrostatic transduction, mechanical transduction, and laser transduction.

16. The method of claim 14, wherein said step of generating an ultrasonic sound includes the step of generating a signal having one of a pulse, a burst, a continuous wave, and a chirp characteristic.

17. The method of claim 13, wherein said step of separating further includes the step of time discriminating said received signal provided said first and said second signal.

18. The method of claim 17, wherein the step of time discriminating includes the step of determining a first and second time interval after the beginning of the step of applying sound energy, and the step of selecting said first and second signal according to said first and second time interval.

19. The method of claim 17, wherein said step of separating includes the step of detecting a flexural component of the propagated acoustic signal.

20. The method of claim 13, further including step of selectively filtering the sensed sound signal.

21. The method of claim 13, further including the step of transferring the acoustic signal through a waveguide.

* * * * *

UNITED STATES PATENT AND TRADEMARK OFFICE
CERTIFICATE OF CORRECTION

PATENT NO. : 4,461,178
DATED : July 24, 1984
INVENTOR(S) : Jacques R. Chamuel

It is certified that error appears in the above—identified patent and that said Letters Patent is hereby corrected as shown below:

Column 1, line 48, "only only the" should read --not only the--;

line 53, "deicings" should read --de-icings--.

Column 4, line 67, "compresional" should read --compressional--.

Column 7, line 21, "portions 134A," should read ---portions 138A,--;

line 66, "modes:" should read --modes;--.

Column 8, line 57, "electromegnetic" should read --electromagnetic--.

Signed and Sealed this

Twenty-third Day of April 1985

[SEAL]

Attest:

DONALD J. QUIGG

Attesting Officer     Acting Commissioner of Patents and Trademarks